(12) United States Patent
Mangosong

(10) Patent No.: US 6,352,530 B1
(45) Date of Patent: Mar. 5, 2002

(54) SLIDEABLE CANNULA AND METHOD OF USE

(75) Inventor: Lorraine Mangosong, Palo Alto, CA (US)

(73) Assignee: Embol-X, Inc., Mountain View, CA (US)

( * ) Notice: Subject to any disclaimer, the term of this patent is extended or adjusted under 35 U.S.C. 154(b) by 0 days.

(21) Appl. No.: 09/616,985

(22) Filed: Jul. 14, 2000

Related U.S. Application Data

(63) Continuation of application No. 09/132,354, filed on Aug. 11, 1998, now Pat. No. 6,129,713.

(51) Int. Cl.[7] .............................................. A61M 31/00
(52) U.S. Cl. ................................... 604/506; 604/509
(58) Field of Search ............................... 604/506–509, 604/164.11, 290, 53, 96, 264

(56) References Cited

U.S. PATENT DOCUMENTS

| | | | | |
|---|---|---|---|---|
| 5,146,925 A | | 9/1992 | Snow | ........................... 128/658 |
| 5,419,777 A | * | 5/1995 | Hofling | ....................... 604/264 |
| 5,681,274 A | * | 10/1997 | Perkins et al. | .................. 604/8 |
| 5,800,484 A | | 9/1998 | Gough et al. | |
| 5,807,318 A | * | 9/1998 | Goar et al. | ................... 604/508 |
| 5,868,702 A | | 2/1999 | Stevens et al. | |
| 5,928,192 A | | 7/1999 | Maahs | |
| 5,931,848 A | | 8/1999 | Saadat | |
| 5,954,694 A | | 9/1999 | Sunseri | |
| 5,980,503 A | | 11/1999 | Chin | ........................... 604/509 |
| 6,048,331 A | * | 4/2000 | Tsugita et al. | ................. 604/96 |
| 6,168,586 B1 | * | 1/2001 | Hahnen | ....................... 604/509 |

* cited by examiner

*Primary Examiner*—Richard K. Seidel
*Assistant Examiner*—Kevin C. Sirmons
(74) *Attorney, Agent, or Firm*—Lyon & Lyon LLP

(57) ABSTRACT

A cannula system having an internally slidable elongate tubular member frictionally anchored within a trocar, and optionally including a flange which acts as a positive stop against the trocar, that can be deployed for various treatments, including aortic cannulation during cardiopulmonary bypass, for example during CABG surgery. The tubular member has a proximal end, a lumen, and a flexible distal end which carries a preformed angled configuration relative to its proximal region and is bendable to a substantially linear configuration. The rigid trocar maintains the cannula in a substantially linear configuration. When the cannula is advanced through the lumen beyond the distal end of the trocar, the tubular member regains its angled configuration. Methods for using the devices herein are also disclosed.

19 Claims, 4 Drawing Sheets

SLIDEABLE CANNULA AND METHOD OF USE

This is a continuation of U.S. Application Ser. No. 09/132,354, filed Aug. 11, 1998, now U.S. Pat. No. 6,129,713, which is expressly and fully incorporated herein by reference.

FIELD OF THE INVENTION

The present invention relates generally to open and/or endoscopic deployment of various devices in body tissues, including a patient's vascular system, using an internally slideable member frictionally anchored within a stationary trocar or introducer. These devices are deployed in various treatments which include balloon occlusion, filtering, aspiration, pressure monitoring, perfusion, and/or cardioplegia delivery.

BACKGROUND OF THE INVENTION

Various cardiothoracic surgeries, including coronary artery bypass grafting (CABG), heart valve repair or replacement, septal defect repair, pulmonary thrombectomy, atherectomy, aneurysm repair and correction of congenital defects, generally require pulmonary bypass (CPB), and cardiac arrest. Traditionally, these surgeries are performed through a mid-stemotomy incision. Such an open chest approach entails prolonged hospitalization and rehabilitation by the patient due to significant trauma to the chest wall. Minimally invasive surgical procedures which use an endoscopic approach have been developed to reduce the morbidity and mortality of the surgery, eliminating the need for a gross thoracotomy. More specifically, small incisions are made on a patient's chest wall, often in the intercostal space, to allow insertion of various instruments to reach the heart and great vessels. In a port-access approach during CABG surgery, arterial cannulation for CPB and cardioplegia delivery for cardiac arrest can be achieved by using endoscopic devices and techniques through a minimal access port in the intercostal space.

New devices and methods are therefore desired to facilitate the performance of minimally invasive CABG. Before CPB can be initiated, incisions are made in the right atrium and the aorta to allow insertion of venous and arterial cannulas. It is often difficult, however, to insert a cannula through various tissue layers to reach the aorta, due to its lack of rigidity. Moreover, it is particularly difficult to insert a cannula having a bent distal end through a narrow intercostal passage into the heart or great vessels. In addition, the cannula may be punctured by the sometimes-calcific arterial wall. A need, therefore, exists for a cannula system which provides easy penetration of a bent cannula through a small incision in tissue layers, and protection of the cannula during its deployment in the aorta.

SUMMARY OF THE INVENTION

The present invention provides less invasive devices and methods for cannulating body tissues and inftising fluid therein. More specifically, the invention provides a cannula system for aortic cannulation and occlusion in preparation for CPB, and cardioplegia delivery for cardiac arrest. This cannula system comprises a cannula having an Elongate tubular member with a proximal end, a flexible distal end, and a lumen therebetween, and a substantially rigid trocar having a proximal end, a distal end, and a lumen therebetween. The distal end of the cannula has a preformed, angled configuration relative to a proximal region, and the angled region is bendable to a substantially linear configuration. The trocar lumen is shaped to receive the elongate tubular member in its linear configuration. The tubular member is slideable through the lumen of the trocar and regains the angled configuration when advanced distally beyond the distal end of the trocar. The preformed, angled configuration of the distal end is typically between 90–140°, in certain instances generally L-shaped, so that after the cannula is deployed in the aorta, its distal end is substantially parallel to the aortic wall and thus allows fluid, such as oxygenated blood from the CPB machine, to be delivered downstream to the aorta.

In another embodiment, the elongate tubular member of the cannula has an additional lumen extending distally from the proximal end and communicating with a balloon occluder mounted at its distal end. The tubular member may also have a cardioplegia lumen and/or a lumen for receiving oxygenated blood from a CPB machine extending distally from its proximal end and communicating, respectively, with a cardioplegia port and/or an infusion port, located proximal or distal the balloon occluder. The proximal end of the tubular member is adapted for attachment to the CPB machine. The distal end of the tubular member may also carry a retractable blade for incising the aorta before the cannula is inserted and may contain a balloon-protecting sleeve.

Alternatively, the trocar may have an additional lumen extending distally from the proximal end and communicating with a balloon occluder mounted at its distal end. The trocar may also have a cardioplegia lumen and/or a lumen for receiving oxygenated blood from a CPB machine, extending distally from the proximal end and communicating, respectively, with a cardioplegia port and/or an infusion port located proximal or distal to the balloon occluder. In addition, the distal end of the trocar may be equipped with a retractable surgical blade for incising body tissue, therefore, facilitating easy penetration into the body tissue. It will be understood that where the cannula carries a cardioplegia lumen, the trocar may carry a lumen for oxygenated blood, and vice versa. Alternatively, in certain embodiments, the cannula-trocar assembly may carry cardioplegia or oxygenated blood, but not both. In still other embodiments, the cannula or the trocar will can-y both cardioplegia and oxygenated blood, and the other will carry neither cardioplegia nor oxygenated blood.

A thin sheath diffuser may be attached to the distal end of the rigid trocar. This allows use of the trocar as an introducer. Instead of or in addition to having a balloon as an arterial occluder, a filter mechanism, made of a semipermeable mesh, may be used to catch aortic plaque emboli, which if allowed to escape downstream, may cause stroke or arterial occlusion of other organs. Alternatively, the balloon occluder may be replaced by a nonpenetrable dam or barrier material deployable on the distal end of the trocar or tubular member.

Another embodiment of the invention provides a slideable cannula system which has a Y-connector attached to the proximal end of the trocar. The Y-connector has an access port and a cannula port. The access port provides insertion of an access mechanism, such as an introducer with a retractable blade, and the cannula port provides insertion of a cannula for fluid and cardioplegia delivery during CABG surgery.

The present invention provides methods for deployment of various devices, including a balloon occluder, an introducer, a filter, an aspirator, a CPB cannula, a light source, a camera, a pressure monitor, an assisting pump, and/or any other devices, into a body tissue. The methods employ a slideable cannula system which has a cannula comprising an elongate member, a proximal end, a distal end, and a lumen therebetween, and a trocar having a proximal end, a distal end, and a lumen shaped to receive the elongate tubular member. The distal end of the cannula has a preformed angle configuration relative to the proximal region. The elongate tubular member is inserted into the trocar followed by insertion of the trocar inserting cannula unit into a body tissue with the trocar maintaining the tubular member in a substantially linear configuration. Alternatively, the trocar is inserted into a body tissue followed by insertion of the elongate tubular member into the lumen of the trocar. The distal end of the tubular member is advanced beyond the distal end of the trocar, wherein the distal end of the trocar member regains its preformed angled configuration.

In minimally invasive CABG surgery, for example, the trocar containing the cannula, as a unit, is introduced through a small port and inserted through various body tissue layers to reach the aorta. In this way, the trocar provides rigidity to the cannula during insertion and protects the cannula, especially the balloon occluder, from being punctured by the sometimes-calcific aortic wall. The methods described above can also be employed in open cardiothoracic surgeries.

In the embodiments where the cannula contains a balloon occluder and a cardioplegia lumen and port, aortic occlusion can be achieved by inflating the balloon occluder and cardioplegic delivery can be achieved through its cardioplegic lumen and port. Alternatively, in the embodiment where the trocar contains the balloon occluder and cardioplegia lumen and port, arterial (particularly aortic) occlusion and cardioplegia delivery can be achieved after the trocar enters the arterial wall. The balloon occluder on the trocar, when inflated, allows positive placement of the occlusion device.

The present invention also provides methods for making an incision in body tissues. In minimally invasive CABG surgery, an aortic incision for CPB cannulation can be achieved by an optional retractable blade carried at the distal end of the rigid trocar. Alternatively, an aortic incision can be achieved by a retractable blade carried at the distal end of the slideable cannula. An access mechanism with surgical blade can also be introduced through the access port of the Y-connector to incise the aorta.

DETAILED DESCRIPTION OF THE INVENTION

Figure 1:
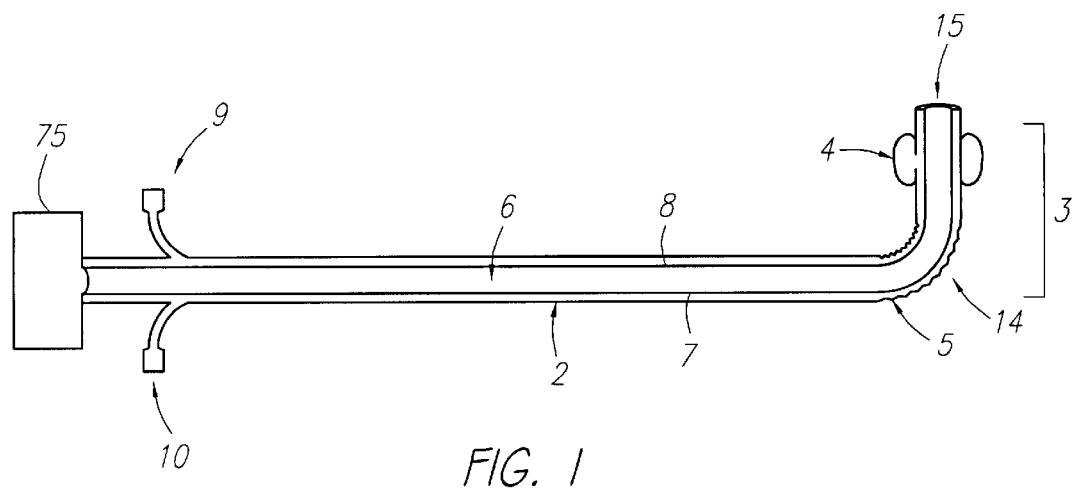
FIG. 1 depicts a cannula having a preformed angled configuration at its distal end.

The devices and methods disclosed herein facilitate deployment of various endoscopic instruments in body tissue, including aortic cannulation for CPB doing minimally invasive CABG surgery. FIG. 1 depicts a preferred embodiment of a cannula having a preformed, angled configuration at its distal end. The cannula has elongate tubular member 2, proximal end 1, and distal end 3. Tubular member 2 has lumen 6 for delivering fluids through end port 15, balloon lumen 8 for inflating balloon occluder 4, and cardioplegia lumen 7 for delivering cardioplegia solution through cardioplegia port 14. Proximal end I has balloon port 9 in communication with balloon lumen 8 for inflating the balloon occluder and cardioplegia entry port 10 in communication with cardioplegia lumen 7 for delivering cardioplegia solution. Distal end 3 of tubular member 2 has a preformed angled configuration of approximately an L-shape. The cannula is bendable at region 5 between the tubular member and its distal end to achieve a substantially linear configuration.

Figure 2:
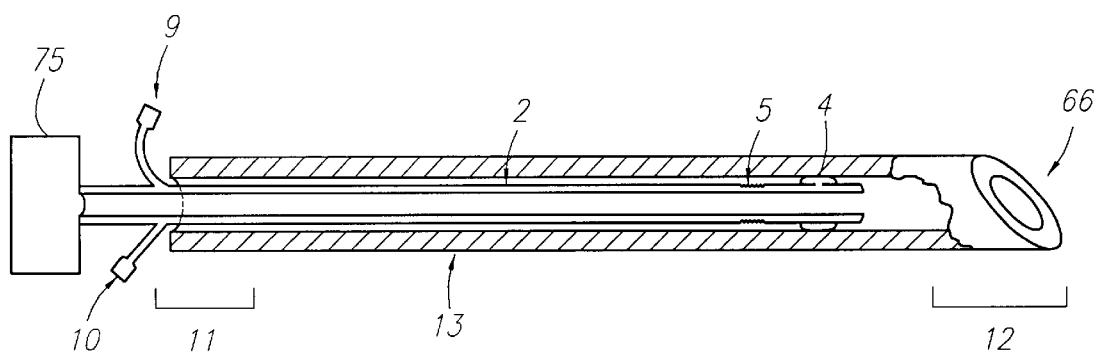
FIG. 2 depicts a cannula inside a rigid trocar having a linear configuration.

FIG. 2 depicts the cannula in FIG. 1 disposed within a rigid trocar, having a linear configuration. The trocar has proximal end 11, distal end 12, and body 13. Tubular body 2 and distal end 3 of the cannula are contained within the trocar, and thereby protected from damage during insertion. Distal end 3 of the cannula is, during insertion, bent at region 5 to have a substantially linear configuration relative to proximal end 1. A thin sheath diffuser 66 may be attached to the distal end 12 of the rigid trocar. The thin sheath diffuser 66 preferably allows use of the trocar as an introducer.

Figure 3:
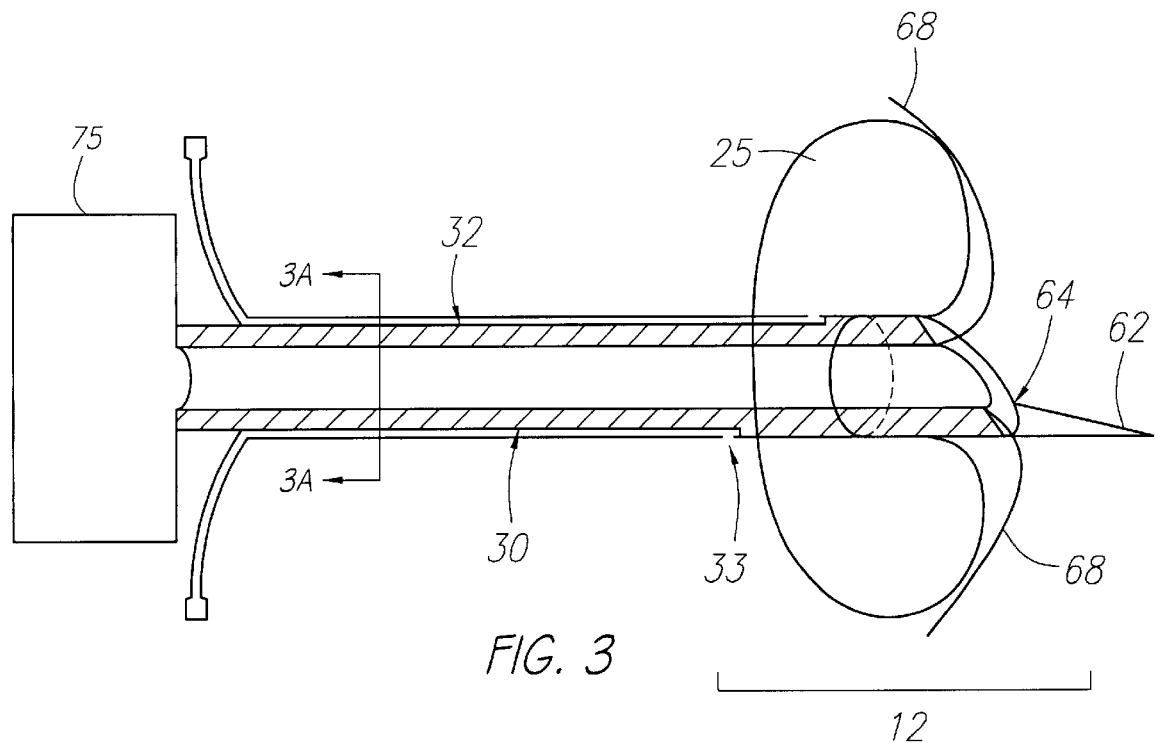
FIG. 3 depicts an alternative embodiment of a rigid trocar having a cardioplegia lumen and a lumen for inflating the distal balloon occluder.
Figure 3A:
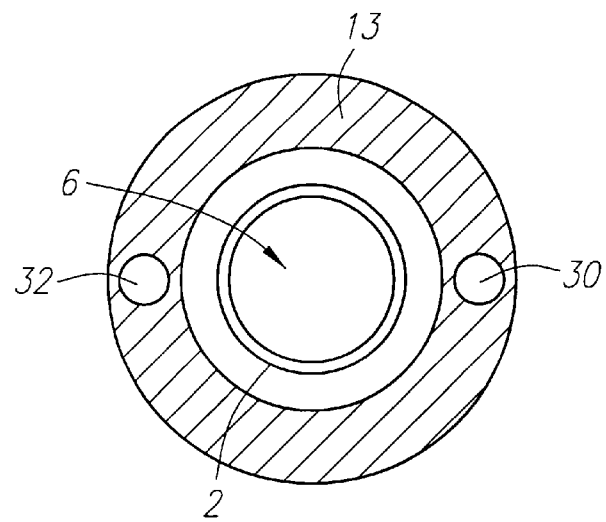
FIG. 3A depicts a cross-sectional view through section line A—A of the slidcable cannula system depicted in FIG. 3.

FIG. 3 depicts an alternative embodiment of a rigid trocar having cardioplegia lumen 30 and balloon lumen 32. Distal end 12 of the trocar has cardioplegia port 33 and balloon occluder 25. This embodiment allows the trocar to function as an aortic occlusion device and a device for cardioplegia delivery for CPB during minimally invasive CABG surgery. The distal end 12 of the trocar may include a retractable surgical blade 62 with a lockout mechanism 64, a balloon-protecting sleeve 68, or both. FIG. 3A depicts a cross-sectional view through section line A—A of the slideable cannula system depicted in FIG. 3.

Figure 4:
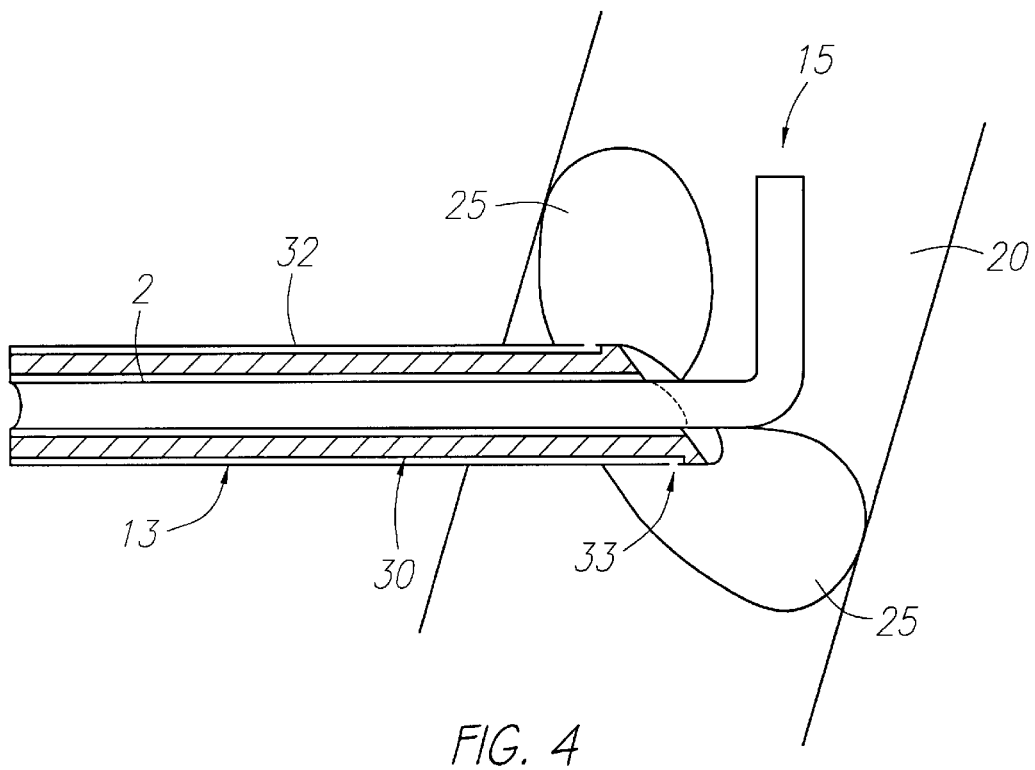
FIG. 4 depicts a cannula having its angled configuration at distal end when deployed inside the aorta.

FIG. 4 depicts a cannula having its angled configuration at the distal end when deployed inside aorta 20. Balloon occluder 25 is inflated to make contact with the aortic wall, thus facilitating positive placement of the cannula. It will be recognized that such an angled orientation of the balloon occluder relative to the aortic wall will permit occlusion while reducing the risk of hyper extension of the aortic walls by balloon over inflation. During minimally invasive CABG surgery, oxygenated blood is delivered by the cannula downstream to the aorta through end port 15 and cardioplegia solution is delivered upstream to the heart through cardioplegia port 33 on the trocar to achieve cardiac arrest. Instead of or in addition to the balloon occluder 25, the distal end of the trocar may include a filter mechanism (not shown) that may be used to catch aortic plaque emboli which, if allowed to escape downstream, may cause stroke or arterial occlusion of other organs. The filter mechanism preferably is made of a semipermeable mesh.

Figure 5:
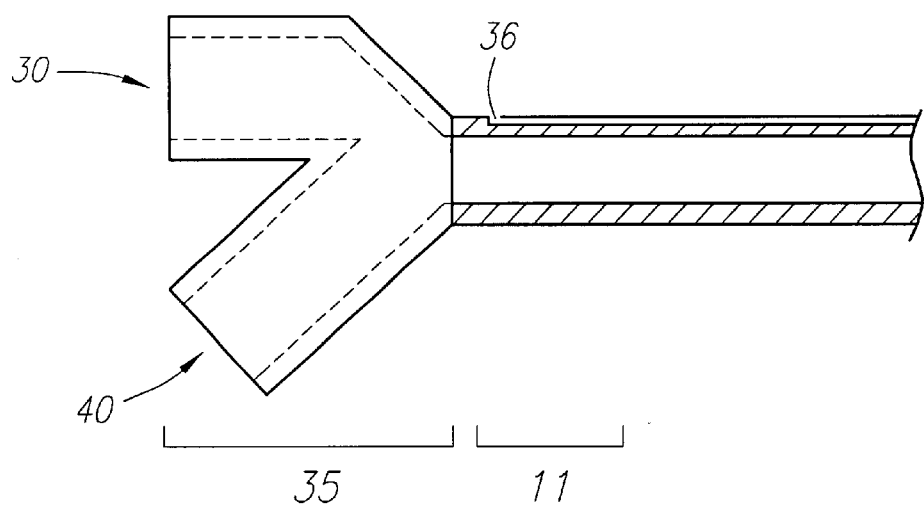
FIG. 5 depicts an alternative embodiment of a rigid trocar attached to a Y-connector.
Figure 6:
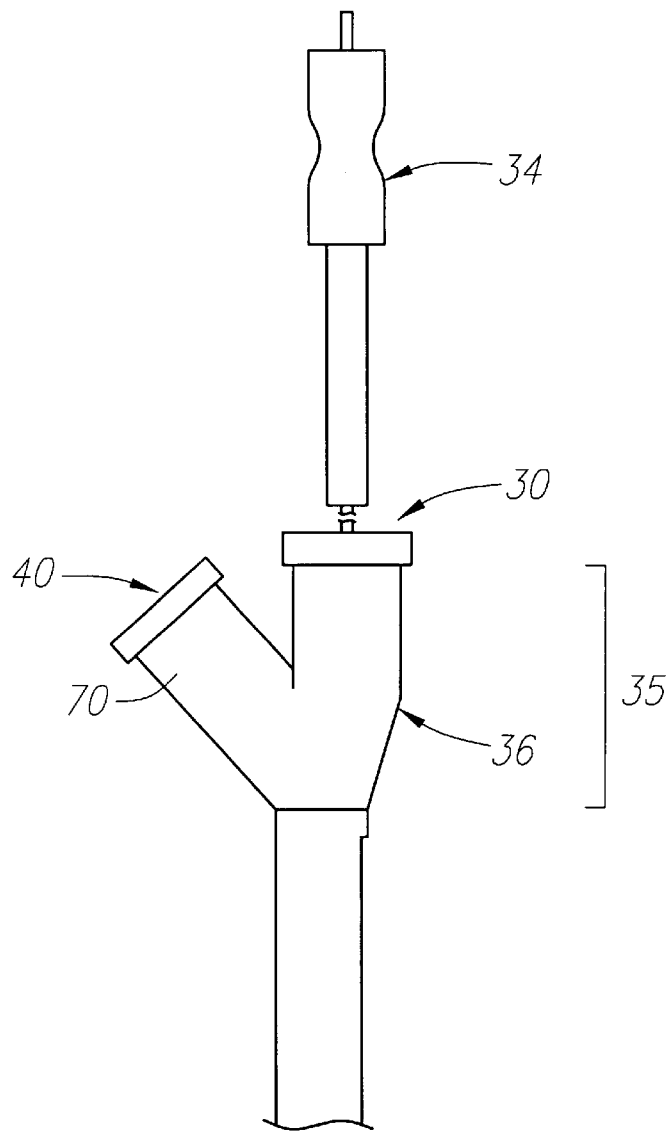
FIG. 6 depicts a side view of the device shown in FIG. 5.

FIGS. 5 and 6 depict an alternative embodiment of a rigid trocar attached to a Y-connector at its proximal end. Y-connector 35 has aortic cannula port 40 and access port 30. Aortic cannula port 40 allows insertion of a cannula to deliver fluid to body tissues, while access port 30 allows insertion of an access mechanism to incise body tissue at the distal end of the trocar. The proximal end of the trocar provides cardioplegia entry port 36 and may further comprise a hemostatic valve 70 at the proximal end of the lumen. FIG. 6 also depicts access mechanism 34 entering access port 30.

Figure 7:
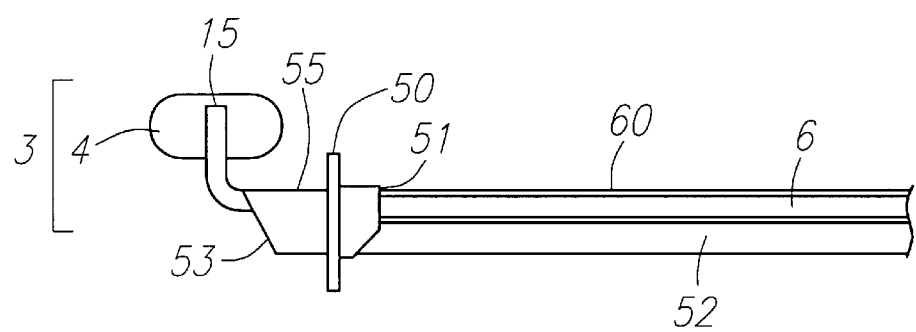
FIG. 7 depicts an alternative embodiment of a trocar having two lumens.

FIG. 7 depicts an alternative embodiment of a trocar which has two lumens. In this embodiment, first lumen 51, which may be relatively short as shown, is used to carry cannula 60 which has a preformed angle configuration at distal region 3, shown here advanced to distal end 55 of the trocar. Cannula 60 has end port 15 and balloon occluder 4, which communicate with lumen 6 and a balloon inflation lumein, respectively. Second lumen 52 of the trocar communicates with infusion port 53. This second lumen can be used to introduce an access mechanism or infuse fluid or blood. The proximal end of cannula lumen 6 or trocar lumen 52 can be adapted for attachment to a cardiopulmonary bypass machine 75. Suture flange 50 is adapted to secure the cannula-trocar assembly on a body tissue, such as by a purse string suture onto the aorta. In CABG surgery, for example, this embodiment can be employed to deliver oxygenated blood to the aorta from a cardiopulmonary bypass machine 75 and cardioplegia solution to the heart to arrest cardiac function. After the trocar is inserted in the aorta balloon occluder 4 is inflated to provide aortic occlusion. When end port 15 is positioned downstream, port 15 can be used to deliver oxygenated blood from a CPB machine 75 to the aorta, and port 53 can be used to deliver cardioplegia upstream to the heart. When end port 15 is positioned upstream, port 15 can be used to deliver cardioplegia to the heart, and port 53 can be used to deliver oxygenated blood from a CPB machine 75 to the aorta to maintain tissue perfusion to the peripheral organs.

The length of the cannula and the trocar will generally be between 5 and 30 centimeters, preferably 15 centimeters. The cross-sectional diameter of elongate member 20 will generally be between 0.2 to 1.5 centimeters, preferably 0.7 centimeters. The cross-section diameter of the trocar body will generally be between 0.5 to 2.0 centimeters, preferably 1.2 centimeters. The luminal diameter of the trocar body will generally be between 0.4 to 1.8 centimeters, preferably 1.0 centimeters. The foregoing ranges arc set forth solely for the purpose of illustrating typical device dimensions. The actual dimensions of a device constricted according the principles of the present invention may obviously vary outside of the listed ranges without departing from those basic principles.

The slideable cannula system and methods disclosed herein can be used for open surgery techniques, but are particularly useful in minimally invasive CABG surgery when a port-access approach is used. During this surgery, a small incision is often made in a patient's intercostal space for placement of an access port. The rigid trocar which contains the slidcable cannula disclosed herein is introduced through the access port and various tissue layers to reach the aorta. Incision in the aorta can be made by (1) a retractable blade (as described in Tsugita et al., U.S. application Ser. No. 08/993,202, filed Dec. 18, 1997) carried on the distal end of the trocar, (2) a retractable blade carried on the distal end of the cannula, (3) an access mechanism introduced through the access port of the Y-connector attached to the proximal end of the trocar, or (4) by any other suitable method.

The trocar, which maintains the cannula in a substantially linear configuration, is inserted into the aorta lumen through the incision. In an embodiment where the trocar carries a balloon occluder and a cardioplegia port, the balloon occluder is inflated to occlude the aorta following the trocar insertion, the cannula is advanced distally beyond the distal end of the trocar to enter the aorta, oxygenated blood from the CPB machine is infused through the lumen of the cannula downstream to the aorta, and cardioplegia solution is delivered upstream to the heart through the cardioplegia port of the trocar to arrest the heart. In certain other embodiments, the lumen and port on the trocar are used to deliver oxygenated blood while the lumen and port on the cannula deliver cardioplegia.

In an embodiment where the cannula carries a balloon occluder and the cardioplegia port, the trocar may be withdrawn after deployment of the cannula or may be maintained in place and used to provide oxygenated blood from a CPB machine. The balloon occluder mounted at the distal end of the cannula is then inflated to occlude the aortic lumen. Oxygenated blood from the CPB machine is infused through the lumen of the cannula downstream to the aorta, and cardioplegia solution is delivered upstream to the heart to arrest the heart. After CPB is initiated and the heart is arrested, the surgeon then proceeds with the revascularization of the heart as described in Reichenspumer et al., *Annals of Thoracic Surgery* 65:413-419 (1998), incorporated herein by reference.

The devices and methods disclosed herein are useful in facilitating cannulation of body tissues for various treatments, such as balloon occlusion (See Barbut et al., PCT Application No. WO97/42879; Tsugita et al., U.S. application Ser. No. 08/854,806, filed May 12, 1997; and Tsugita et al., U.S. application Ser. No. 08/993,202, filed Dec. 18, 1997, incorporated herein by reference), filtering (See Barbut et al. U.S. Pat. No. 5,769,816, incorporated herein by reference, Barbut et al., PCT Application No. WO97/17100 and Barbut U.S. application Ser. No. 08/842,727, filed Apr. 16, 1997, incorporated herein by reference), aspiration (See Maahs, U.S. application Ser. No. 08/899,606, filed Jul. 24, 1997, incorporated herein by reference), perfusion, pressure monitoring, and/or cardioplegia delivery. In addition to minimally invasive CABG surgery, the devices and methods herein can be employed in a similar fashion described above in a variety of cardiothoracic surgeries, which include thoracic aortic aneurysm repair, septal defect repair, and valvular repair where CPB is indicated. In various pediatric surgeries, such as atrial septal defect, tiLncous arteriosis, tetrology of Fallot, analomous coronary artery, Ebsteini's malformation of the tricuspid valve, heart/lung transplantation, and total analomous pulmonary vein repair, CPB is commonly indicated postoperatively due to a low cardiac output state. The slideable cannula system can easily be left in place postoperatively to provide easy access to CPB. The devices and methods herein may also be useful in other noncardiac surgeries, such as abdominal aortic aneurysm repair and atherectomy of femoral arteries.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for cannulating an artery, comprising the steps of:
   providing a slideable cannula comprising an elongate tubular member having a proximal end, a distal end, and a lumen therebetween, the distal end comprising a coitugated region and having a preformed angled configuration relative to the proximal end, the slideable cannula further comprising a trocar having a proximal end, a distal end, and a lumen shaped to receive the elongate tubular member;

inserting the elongate tubular member into the lumen of the trocar, the trocar maintaining the tubular member in a substantially linear configuration;

inserting the trocar through an incision in an artery; and advancing the distal end of the tubular member beyond the distal end of the trocar into the artery, wherein the distal end of the tubular member regains its preformed angle configuration.

2. The method of claim 1, wherein the step of inserting the elongate tubular member into the lumen of the trocar is performed before the step of inserting the trocar into a vessel.

3. The method of claim 1, wherein the artery is an aorta.

4. The method of claim 1, wherein the artery is a carotid artery.

5. The method of claim 4, wherein the artery is a femoral artery.

6. The method of claim 5, further comprising the step of making an incision in the aorta using the trocar.

7. The method of claim 5, further comprising the step of making an incision in the aorta using the cannula.

8. The method of claim 1, wherein the slideable cannula further includes a cardioplegia lumen communicating with a cardioplegia port, and wherein the method further comprises the step of delivering cardioplegia solution through the cardioplegia port.

9. The method of claim 1, further comprising the step of connecting the proximal end of the cannula to a cardiopulmonary bypass machine.

10. The method of claim 1, further comprising the step of connecting the proximal end of the trocar to a cardiopulmonary bypass machine.

11. The method of claim 1, further comprising the step of performing cardiopulmonary bypass.

12. The method of claim 1, further comprising the step of performing a coronary artery bypass graft procedure.

13. The method of claim 1, wherein the step of providing a slideable cannula includes providing a trocar having a balloon occluder mounted on the distal end of the trocar.

14. The method of claim 13, wherein the balloon occluder communicates with the proximal end of the trocar.

15. A method for cannulating, an artery, comprising the steps of:

providing a slideable cannula comprising an elongate tubular member having a proximal end, a distal end, and a lumen therebetween, the distal end having a corrugated region and a preformed angled configuration relative to the proximal end, the slideable cannula further comprising a trocar having a proximal end, a distal end, and a lumen shaped to receive the elongate tubular member;

inserting the elongate tubular member into the ILIIImCIn of the trocar, the trocar maintaining the tubular member in a substantially linear configuration;

inserting the trocar into the aorta; and advancing the distal end of the tubular member beyond the distal end of the trocar into the aorta, wherein the distal end of the tubular member regains its preformed angle configuration.

16. The method of claim 15, further comprising the step of making an incision in the aorta using the trocar.

17. The method of claim 15, further comprising the step of making an incision in the aorta using the cannula.

18. The method of claim 15, wherein the slidcable cannula further comprises a cardioplegia lumen communicating with a cardioplegia port, and wherein the method further comprises the step of delivering cardioplegia solution through the cardioplegia port.

19. The method of claim 15, wherein the trocar is inserted into the aorta through an incision in the aorta.

* * * * *

UNITED STATES PATENT AND TRADEMARK OFFICE
CERTIFICATE OF CORRECTION

PATENT NO.    : 6,352,530 B1
DATED         : March 5, 2002
INVENTOR(S)   : Mangosong It is certified that error appears in the above-identified patent and that said Letters Patent is hereby corrected as shown below:

Title page,
Item [56], References Cited, add:

-- FOREIGN PATENT DOCUMENTS
764784          9/1980          (SU) --

Column 6,
Line 63, change "coitugated" to -- corrugated --.

Column 8,
Line 16, change "ILIIImCIn" to -- lumen --.

Signed and Sealed this

Tenth Day of September, 2002

Attest:

JAMES E. ROGAN
Attesting Officer    Director of the United States Patent and Trademark Office